United States Patent [19]

Panster et al.

[11] Patent Number: 4,578,496

[45] Date of Patent: Mar. 25, 1986

[54] POLYMERIC METAL-AMINE COMPLEX COMPOUNDS, PROCESSES FOR THEIR PREPARATION AND USE

[75] Inventors: Peter Panster, Rodenbach; Peter Kleinschmit, Hanau, both of Fed. Rep. of Germany

[73] Assignee: Degussa Aktiengesellschaft, Frankfurt, Fed. Rep. of Germany

[21] Appl. No.: 543,720

[22] Filed: Oct. 20, 1983

Related U.S. Application Data

[62] Division of Ser. No. 404,115, Aug. 2, 1982, Pat. No. 4,424,332.

[30] Foreign Application Priority Data

Aug. 13, 1981 [DE] Fed. Rep. of Germany ....... 3131954

[51] Int. Cl.$^4$ .................. C07F 7/08; C07C 69/02; C07C 45/00; C07C 5/02
[52] U.S. Cl. .................. 556/479; 560/231; 568/451; 585/275; 585/276; 585/277
[58] Field of Search .................. 556/479; 568/451; 560/231; 585/277, 275, 276

[56] References Cited

U.S. PATENT DOCUMENTS 4,424,332 1/1984 Panster et al. .................. 528/30

Primary Examiner—Paul F. Shaver
Attorney, Agent, or Firm—Beveridge, DeGrandi & Weilacher

[57] ABSTRACT

Polymeric complex compounds of molybdenum, tungsten, manganese, rhenium and of the metals of the subgroups VIII and I of the Periodic Table of Elements, which complex compounds have a silica-type structure are disclosed. At least one amine

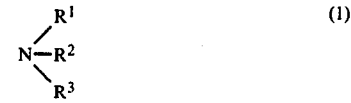

is bonded coordinately to the central metal atom. The atomic ratio of metal to nitrogen is from 1:1 to 1:10$^6$. The required charge compensation is effected by means of an anion. In (1), R$^1$ and R$^2$ represent a group

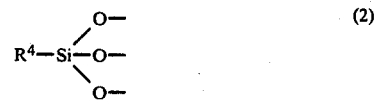

and R$^4$ is an alkylene grouping. The oxygen atoms are saturated by silicon atoms of further groups (2), if appropriate with incorporation of crosslinking agents. R$^3$ may have the meaning of R$^1$ and R$^2$, or represents hydrogen, an alkyl group, a cycloalkyl group or the benzyl group. The polymers can contain several metals. The invention also relates to processes for their preparation, and uses in catalysis.

11 Claims, No Drawings

POLYMERIC METAL-AMINE COMPLEX COMPOUNDS, PROCESSES FOR THEIR PREPARATION AND USE

This application is a division of application Ser. No. 404,115 filed Aug. 2, 1982, now U.S. Pat. No. 4,424,332.

The invention relates to novel polymeric coordination compounds of metals of sub-groups VI, VII, VIII and I of the Periodic Table, which contain polymeric, silicon-substituted amines as ligands, to processes for their preparation and to the use of these heterogeneous metal complexes as catalysts.

It is known that the use of so-called homogeneous catalysts in industry is associated in particular with the problems of separating off and recycling the catalyst, the recovery of the metal, which in most cases is valuable, the predominantly short service life of these materials, and the frequently extensive corrosion of the production plant by the metal compounds, some of which are salt-like. Intensive efforts have therefore already been in progress for some time, with the aim of avoiding these disadvantages of homogeneous catalysts, and combining the advantages of the homogeneous and heterogeneous catalysts in so-called heterogenized catalysts. These consist of metal units which are in principle soluble and which are bonded to carriers by covalent, ionic or adsorptive interactions. The prior art in this field has already been summarized in several review articles, for example also by R. H. Grubbs in CHEMTECH, August 1977, page 512, or by D. D. Whitehurst in CHEMTECH, January 1980, page 44. The carrier materials employed hitherto were, in particular, organic polymers which, in most cases only after suitable modification, for example in the case of polystyrene, by primary introduction of chloromethyl groups, are capable of fixing soluble metal complex catalysts. The heterogenization of metal complexes using organic polymers as carriers is described, for example, by R. H. Grubbs and L. C. Kroll in J. Amer. Chem. Soc. 93, 3,062 (1971), by M. Capka et al in Tetrahedron Letters 1971, 4,787, and also in British Pat. No. 1,277,737.

However, the organic polymers used as carrier materials in general do not at all possess the qualities required of a good catalyst carrier, since they do not possess a fixed structure, and their conformation and therefore their surface area, as well as the volume of the individual particle, are strongly dependent on external parameters, such as temperatures, pressure and solvent. It is a constant requirement that the carrier should swell in the solvent used, in order to make it possible for the reactants to penetrate to the centers of catalysis, and to prevent the reaction rate from becoming diffusion-controlled. The high mobility of the matrix also allows fixed metal units to come together, so that the undesirable formation of catalytically inactive multi-nuclear complexes becomes possible, and, in addition, it is possible for carrier-bound, non-coordinated ligands to block the catalytically active metal center (cf. G. Strukul, P. D'Olimpio, M. Bonivento, F. Pinna and M. Graziani in J. Mol. Catal. 2, 179 (1977)). It is also possible for the polymeric organic matrix to be soluble in those solvents which were per se advantageous for the catalytic reaction.

In comparison, inorganic polymer systems, such as, for for example, precipitated or pyrogenic silica possess a fixed structure and a much higher thermal stability and resistance to aging, and, in addition, the fixed metal units are located, readily accessible, at the surface. It is therefore understandable that inorganic carriers have already been used for the fixation of homogeneous catalysts, as described, for example, in U.S. Pat. No. 4,083,803, in German Offenlegungsschrift No. 2,062,351, or by H. H. Brintzinger et al. in J. Organomet. Chem. 148, 73 (1978). However, inorganic carrier materials have a serious disadvantage in that the number of hydroxyl groups, via which a bond to the ligand or to the metal atom can be effected, is relatively small, so that a large number of ligands or metal atoms cannot be carried, and a large amount of carrier ballast is carried around with the catalyst.

Recently, it has been possible, as described in U.S. patent application Ser. No. 063,291 filed Aug. 2, 1979 and U.S. patent application Ser. No. 283,868 filed July 16, 1981, the entire disclosure of each of which is relied on to find a novel principle, according to which it is possible to heterogenize homogeneous sulfide and phosphine complex catalysts of the metals rhodium, iridium and ruthenium, without the use of a carrier. The polymeric carrier, synthesized from intramolecularly and intermolecularly formed siloxane units, is produced by hydrolysis and condensation of the trialkoxy, triphenoxy or trihalosilyl units present on the ligands.

As expected, it also exhibits the above-mentioned good properties of inorganic carriers, and, in addition, can be made to measure, for example in respect of the very important aspects relating to the possibility of incorporating in the matrix more or less ligands than are required by the stoichiometry of the complex to be heterogenized, or so-called crosslinking agents, by means of which it is possible to control the density of catalysis centers in the solid, as well as so-called activators or co-catalysts. However, compared to systems based on inorganic carriers, these silica type polymeric systems possess, in particular, the advantages that they are able to contain a higher metal concentration at the same ligand:metal ratio, that they are simpler to prepare, and that they are more resistant to hydroxides owing to the strongly hydrophobic character of the matrix.

We have now been able to show that, according to the concept of the polycondensation of ligands which are substituted by trifunctional silicon, it is possible to obtain not only polymeric rhodium, iridium and ruthenium sulfide or phosphine complexes, but also a wide range of polymeric amine complexes of molybdenum, tungsten, manganese, rhenium and the metals of sub-groups VIII and I of the Periodic Table, which complexes are very useful for catalysis, and have a wide variety of uses and activities. Particularly important among these complexes are the rhodium, iridium, ruthenium, palladium and platinum compounds as well as the cobalt compounds. In the case of these types of heterogenized complex catalysts, also, it has been possible to obtain the specific and ligand-typical properties present in comparable monomeric systems. Likewise, as in the case of the sulfide and phosphine systems, the polymeric matrix possesses the above-mentioned excellent properties in this case as well.

In the novel polymeric amine complexes of molybdenum tungsten, manganese, rhenium and the metals of sub-groups VIII and I of the Periodic Table, having a silica type structure, at least one amine of the general formula:

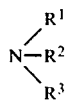 (1)

is bonded coordinately to the central metal atom, the metal:nitrogen atomic ratio is from 1:1 to 1:10$^6$, any coordination points at the metal atom which are still free are occupied by other electron pair donors, such as, for example, carbon monoxide, nitric oxide, triphenylphosphine, triphenylarsine, phosphite, linear or branched alkyl groups containing a secondary or tertiary alkylamine having 1 to 5 C atoms, benzylamine, dialkyl sulfide, olefin, diolefin, acetylene, nitrile, isonitrile, cyanate, isocyanate or water (water of crystallization), and the required charge compensation is effected by an inorganic or organic anion, such as a chloride, bromide, iodide, nitrate, sulfate, phosphate, acetylacetonate, acetate, trifluoroacetate, trichloroacetate, propionate, methylate, ethylate, propylate, butylate, phenylate, perchlorate, tetraphenyl borate, hexafluoro phosphate, methyl-, ethyl-, propyl-, butyl-, phenyl- or perfluorophenyl ion, if appropriate with complete or partial replacement of such anions by hydride ions, and, in formula (1), R$^1$ and R$^2$ represent a group of the general formula:

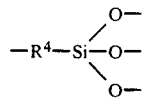 (2)

R$^4$ denotes a linear or branched alkylene group having 1 to 10 C atoms or a cycloalkylene group having 5 to 8 C atoms, or represents the units

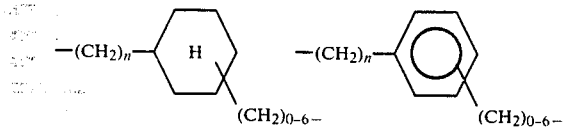

wherein n is 1 to 6 methylene groups linked to a nitrogen atom, R$^1$ and R$^2$ can be identical or different, and the free valences of the oxygen atoms are saturated either by silicon atoms of further groups of the formula (2) and/or by crosslinking bridge members

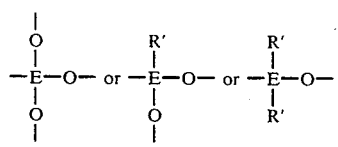

wherein E represents silicon, titanium or zirconium, or by

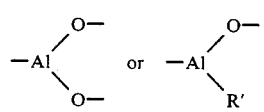

wherein R' is a methyl or ethyl group, and the ratio of the silicon atoms in (2) to the bridge atoms silicon, titanium, zirconium and aluminum can be from 1:0 to 1:10, and R$^3$ has the same general meaning as R$^1$ and R$^2$, or represents hydrogen, a linear or branched alkyl group having 1 to 10 C atoms or a cycloalkyl group having 5 to 8 C atoms or the benzyl group.

The monomeric intermediates of the amines of the formula (1) and also the polymeric amines themselves can be prepared by conventional processes, for example according to the instructions of U.S. patent application Ser. No. 376,882 filed May 10, 1982, the entire disclosure of which is relied on herein. The composition of the monomeric intermediates may be described, for example by formulae such as:

(H$_3$C)N[CH$_2$CH$_2$CH$_2$Si(OC$_2$H$_5$)$_3$]$_2$, (C$_6$H$_5$CH$_2$)N[CH$_2$CH$_2$CH$_2$Si(OC$_2$H$_5$)$_3$]$_2$, (H$_3$C)N[CH$_2$Si(OC$_2$H$_5$)$_3$]$_2$,

N[CH$_2$CH$_2$CH$_2$Si(OC$_2$H$_5$)$_3$]$_3$ and

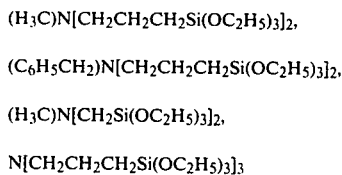

and the composition of the corresponding polymeric amines may be described by formulae such as:

(H$_3$C)N(CH$_2$CH$_2$CH$_2$SiO$_{3/2}$)$_2$, (C$_6$H$_5$CH$_2$)N(CH$_2$CH$_2$CH$_2$SiO$_{3/2}$)$_2$, (H$_3$C)N(CH$_2$SiO$_{3/2}$)$_2$,

N(CH$_2$CH$_2$CH$_2$SiO$_{3/2}$)$_3$ and

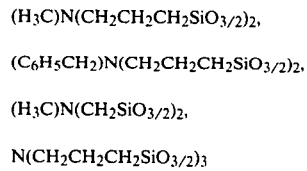

The stoichiometric composition of the polymeric transition metal complexes prepared using the amine ligands of the general formula (1) can be described by formulae such as MoX$_4$L$_{1-10^6}$, MoX$_5$L$_{1-10^6}$, Mo(CO)$_{3-5}$L$_{1-10^6}$,
WX$_4$L$_{1-10^6}$, WX$_6$L$_{1-10^6}$ and W(CO)$_{3-5}$L$_{1-10^6}$ in the case of molybdenum and tungsten, by formulae such as MxXL$_{1-10^6}$, MnX$_2$L$_{1-10^6}$, ReX$_3$L$_{1-10^6}$,
ReX$_4$L$_{1-10^6}$, ReX$_5$L$_{1-10^6}$ and ReX$_6$L$_{1-10^6}$ in the case of manganese and rhenium, by formulae such as FeXL$_{1-10^6}$, FeX$_2$L$_{1-10^6}$, FeX$_3$L$_{1-10^6}$, Fe(CO)$_{3-4}$L$_{1-10^6}$, CoXL$_{1-10^6}$, CoX$_2$L$_{1-10^6}$, CoX$_3$L$_{1-10^6}$, Co$_2$(CO)$_{6-7}$L$_{1-10^6}$, NiXL$_{1-10^6}$, NiX$_2$L$_{1-10^6}$, Ni(CO)$_{2-3}$L$_{1-10^6}$,
RuX$_2$L$_{1-10^6}$, RuX$_3$L$_{1-10^6}$,
RhXL$_{1-10^6}$, RhX$_2$L$_{1-10^6}$, RhX$_3$L$_{1-10^6}$,
PdXL$_{1-10^6}$, PdX$_2$L$_{1-10^6}$, PdX$_4$L$_{1-10^6}$,
OsX$_4$L$_{1-10^6}$, OsHXL$_{1-10^6}$, $IrXL_{1-10^6}$, $IrX_3L_{1-10^6}$,
$PtX_2L_{1-10^6}$ and $PtX_4L_{1-10^6}$ in the case of the metals of sub-group VIII of Periodic Table, and by formulae such as $CuXL_{1-10^6}$, $CuX_2L_{1-10^6}$, $AgXL_{1-10^6}$, $AuXL_{1-10^6}$ and $AuX_3L_{1-10^6}$ in the case of the metals of sub-group I, wherein L represents at least one ligand of the formula (1), and otherwise represents another electron pair donor, and X denotes a monovalent, divalent or trivalent anion.

In addition to the ligands L of the formula (1) which belong to the immediate coordination sphere of the metal, it is possible for further non-coordinated ligands L of the formula (1) to be present in the polymeric matrix, which may contain crosslinking agents, these further ligands being present in an amount such that the metal:nitrogen atomic ratio is not more than $1:10^6$.

In addition, it is possible for different types of complexes of different metals to be present along side one another on the polymeric amine (maximum 16), representing very useful and active mutli-metal catalyst systems.

Particularly preferred compounds within the large range of novel metal complex systems which can be prepared are the polymeric complex compounds in which X represents chloride, bromide, iodide, nitrate, acetate, sulfate, carbonate, phosphate, acetylacetonate or hydride, and L exclusively represents ligands of the formula (1).

Some of the other above mentioned types of complex can be obtained only after the starting polymers have been subjected to chemical modification which can or must be carried out with a view to achieving a further improvement in the activity or selectivity of the heterogenized homogeneous catalyst. This modification comprises a reduction in the oxidation state of the metal atom, partial or complete substitution of the anions X by other anions, or the additional introduction of further anions or of ligands, such as, for example, triphenylphosphine, which are not bonded to the matrix. In practice, this employs a reaction of the polymeric metal complex systems with $H_2$ or CO, or $H_2$ plus CO, or with reducing agents or with Lewis acids, or the introduction of another anion, or reaction with additional ligands under total pressures of from 1 to 3,000 bar and at temperatures from $-100°$ to $350°$ C.

Conventionally used reducing agents are formaldehye, hydrazine, alkali metal borohydrides or alkaline earth metal borohydrides, borane compounds, aluminum hydrides, aluminum alkyls or even just alcohols.

To introduce another anion, it is possible to employ compounds such as alkali metal alkylates (eg. an alkali metal methylate, ethylate or propylate), alkali metal phenylates or alkali metal alkyls or phenyls or sodium acetate, sodium acetylacetonate or sodium iodide.

For a reaction with additional ligands, it is possible to employ compounds such as triphenylphosphine, triphenylarsine, linear or branched alkyl groups containing secondary or tertiary alkylamines having 1 to 5 C atoms, benzylamine, dialkysulfides or even olefins or diolefins.

The invention also relates to a process for the preparation of these polymeric metal-amine complex compounds which are sparingly soluble or insoluble in organic solvents. The process comprises, in particular, reacting a ready-prepared polymeric amine of the formula (1) which may contain crosslinking agents of the stated type with at least partially dissolved compounds of one or more of the prescribed metals, which compounds may contain chloride, bromide, iodide, nitrate, acetate, sulfate, carbonate, phosphate, acetylacetonate or hydride and/or, if appropriate ligands, such as water of crystallization, carbon monoxide, amine, triphenylphosphine, phosphite, sulfide, olefin, acetylene, nitrile, isonitrile, cyanate or isocyanate, if appropriate with displacement of one or more ligands, at room temperature or an elevated temperature of up to $350°$ C., under atmospheric pressure or an elevated pressure corresponding to the sum of the partial pressures of the individual components of the reaction mixture at the particular temperature, and then separating off the metal-containing polymeric solid from the liquid phase by distillation, filtration, centrifuging and/or decanting, washing or extracting it, if appropriate, with water or an organic solvent, then drying it at temperatures from room temperature to $200°$ C., if appropriate heating it over a period of from 1 hour to 4 days at temperatures of from $200°$ to $400°$ C., and then, if appropriate, grinding it and/or classifying it.

The choice of the solubilizers or solubilizer mixtures which may be used for the reaction of the polymeric amine with the metal compounds is not particularly critical, since all solubilizers are suitable which are capable of dissolving the metal component at least partially, and, in addition, do not impede their fixing by effecting strong coordinate interactions or having a reducing or oxidizing effect. In the case of the in situ preparation of the polymeric amine described in U.S. patent application Ser. No. 376,882 filed May 10, 1982, a solubilizer, such as, for example, an alcohol, should be used at the outset, and may also be employed, as a mixture with water, for the further reaction with the metal component. Suitable liquids for the reaction medium are, in general, water, methanol, ethanol, n- and i-propanol, n-, i- and t-butanol, n-pentanol, dioxane, nitromethane, nitrobenzene, ethylene glycol monomethyl ether, ethylene glycol dimethyl ether, diethylene glycol dimethyl ether, ethylene glycol, acetone, tetrahydrofuran, dimethylformamide, dimethylsulfoxide, benzene, toluene, cyclohexane, methylcyclohexane, n-hexane, chloroform and methylene chloride, or mixtures of these. However, polar solvents, such as alcohols or alcohol/water mixtures, are preferred in most cases.

Using the process according to the invention, it is also possible to prepare polymeric multi-metal-amine complexes, i.e. mixed polymeric sparingly soluble or insoluble compounds of two or more of the metals molybdenum, tungsten, manganese, rhenium and the metals of sub-groups VIII and I of the Periodic Table. Using an advantageous embodiment of the process according to the invention, it is possible to react a polymeric amine of the formula (1), which may contain a crosslinking agent, simultaneously or successively with different compounds, which are at least partially dissolved, of the prescribed metals, in the manner described, the metal-containing solid being separated off from the liquid phase, if appropriate after each reaction, by distillation, filtration and/or decanting, washed or extracted, dried and, if appropriate, heated.

To obtain polymeric multi-metal-amine complexes, it is thus possible to fix two or more compounds of two or more metals along side one another on the same polymeric amine, either by simultaneously reacting the polymeric amine with the metal starting compounds under the conditions described, or by carrying out the reaction in several successive steps, and the polymeric solid can be subjected in each case to some or all of the working-up measures mentioned. At the end of a synthesis, the multi-metal system obtained may be used either while still in the reaction medium or after it has been separated off, washed or extracted, dried, if appropriate heated, ground and/or classified, it being possible to omit one or more of these measures under certain circumstances.

The polymeric complex compounds containing one or more metals can be further modified by after-treating them, preferably while suspended in a solvent, once or several times with $H_2$ or $CO$, or $H_2$ plus $CO$, or with reducing agents or with Lewis acids, or by introducing another anion, or by reaction with additional ligands under total pressures of from 1 to 3,000 bar and at temperatures of from $-100°$ to $350°$ C. Depending on the treatment agent chosen, this modification can be effected even in the reaction medium, or after carrying out one or more of the treatment steps isolation, drying and heating. The modification may even be carried out while the complexes are being used for a particular purpose.

A modification step can, for example, comprise treating the solid to be treated, while mixing vigorously, if appropriate in the presence of a solubilizer, with a stoichiometric or excess amount of a reactant, which is present as the pure substance and may be in gaseous or dissolved form, under the prescribed pressure and temperature conditions.

If only one starting component of polymeric mutli-metal-amine complexes is to be modified, it is most advantageous to apply this starting component first to the polymeric amine and thereafter, if appropriate after prior isolation, drying and change of solubilizer, to carry out the appropriate treatment before further metal compounds are applied onto the polymeric amine carrier. In some cases, however, it is also possible to carry out a joint treatment of complete multi-metal starting systems.

A further process for the preparation of the novel polymeric metal-amine complexes, which cannot be used over such a wide range owing, in particular, to the fact that many metal systems can be readily reduced, comprises using a monomeric intermediate of an amine according to formula (1) to initially form a monomeric metal-amine complex system in solution or as pure substance, in which complex system, if appropriate, still further electron pair donors are located at the central atom, and the monomeric intermediate of the amine may be present in an amount which is in excess of that required by the stoichiometry of the desired complex compound. Simultaneously or subsequently, where relevant after a change of solvent and/or the addition of crosslinking agents, such as $Si(OR)_4$, $R'Si(OR)_3$, $R_2'Si(OR)_2$, $Ti(OR)_4$, $R'Ti(OR)_3$, $R_2'Ti(OR)_2$ $Zr(OR)_4$, $R'Zr(OR)_3$, $R_2'Zr(OR)_2$ or $Al(OR)_3$ or $R'Al(OR)_2$, wherein R represents an alkyl group containing 1-5 C atoms and R' represents a methyl or ethyl group, the monomeric metal-amine complex system is reacted, at or above the boiling point of the solvent used, with water or an aqueous acid solution, where relevant with simultaneous or subsequent removal of the resulting alcohol by distillation, and a polycondensate is obtained thereby. The solid polycondensate is then treated in suspension, preferably at an elevated temperature, and is then freed of solvent by distillation, filtration, centrifuging and/or decanting. It is then washed or extracted with the same solvent or with another solvent. This is followed by the drying step at temperatures from room temperatures to $200°$ C. If appropriate, the dry material can be heated for a period of from 1 hour to 4 days at temperatures of from $200°$ to $400°$ C. The heated product may be ground and/or classified.

As an alternative to this two-stage procedure, it is also possible in some cases to add excess water or excess aqueous acid solution to the solvent used, even before the in situ preparation of the monomeric complex compound, since the amine substituted by trifunctional silicon undergoes polycondensation more rapidly in the coordinated state than in the non-coordinated state owing to its steric arrangement in the complex, so that the desired polymeric insoluble coordination compound is precipitated quantitatively in the course of the reaction.

Using this principle of synthesis, the initially obtained polymeric metal-amine complex can be modified directly, without further isolation, in the above mentioned solvent mixture, according to the modification methods already discussed, and can then either be used directly or first separated off from the liquid phase, if appropriate by distillation, filtration and/or decanting, washed or extracted, dried, if appropriate heated, and ground and/or classified.

In principle, it is also possible, instead of the alkoxy derivatives of the silyalkylamines used, or of the crosslinking agents employed, to use the corresponding phenoxy or halo representatives, although the preparation of some of them is more expensive and/or their use involves complications, owing to the phenol or hydrogen halide liberated in the hydrolysis.

Although the surface and particle structure of the polymers may be influenced by the choice of the preparation process and its parameters, the preparation procedure described initially is in general to be regarded as the most suitable.

With regard to their physical properties, the polymeric metal-amine complexes according to the invention behave as special silicas or silica gels, and possess, depending on the pretreatment, specific surface areas of from 0.1 to 3,000 $m^2/g$ and particle diameters of from about 1 cm to about 1 μm. Some of the complexes are stable up to over $200°$ C. in air. Under a protective gas atmosphere, the thermal stability is substantially higher, some of the compounds being stable up to above $400°$ C. Their high abrasion resistance permits them to be used in all conventional catalysis process technology.

The polymeric coordination compounds, according to the invention, of molybdenum, tungsten, manganese, rhenium and the metals of sub-groups VIII and I of the Periodic Table represent valuable catalysts for chemical reactions, such as hydroformylation, hydrogenation, hydrosilylation, oligomerization, carbonylation, carboxymethylation, isomerization, metathesis and oxidation reactions, and for reactions of CO with $H_2$. It is of course obvious to the skilled worker that not all of the metals mentioned are suitable as catalysts for the same reaction, but that each metal or each metal combination has its specific field of use.

For example, the hydroformylation of olefin can be carried out using the novel polymeric rhodium-amine and cobalt-amine complexes, in a manner which is known per se, under hydrogen/carbon monoxide total pressures of from 1 to 1,000 bar and at temperatures from room temperature to $280°$ C., with or without the use of a solubilizer, a high catalyst activity and catalyst selectivity permitting the exclusive formation of aldehydes and, even under relatively mild conditions in the case of the rhodium derivatives, also the formation of the corresponding alcohols.

Hydrogenation of olefinic or acetylenic compounds can be carried out at room temperature or an elevated temperature, under reduced pressure, atmospheric pressure or elevated pressure. In this process, in particular complexes modified by furthr ligands develop a considerable selectivity. The activities achievable are comparable with corresponding homogeneous catalyst systems; in respect of the service life and the case of separation of constituents of the reaction mixture, such as the solvent, substrate residues and the product, the polymeric complexes according to the invention, however, possess substantial advantages. After they have been separated off, they may be used again, without any loss in activity being detectable.

The invention is illustrated further by the examples below. The special polymeric amine ligands L of the formula (1) which, in these examples, are used according to the invention in the individual complex systems, represent simple and readily obtainable representatives of their type, and accordingly are used as models. This statement is justified, in particular, by the generally known properties of organosilicon compounds of this type, and also by the fact that the polymeric amines of the novel complexes are not substantially different in respect of their ligand qualities in comparison with the monomeric amines, so that this principle of the polycondensation of trialkoxysilyl-functional amines can be extended, for suitable functionalization, to virtually all amine ligands which are known and have already been used. The same also applies, of course, to the anion X employed.

EXAMPLE 1

10 g of a finely ground polymeric amine, consisting of units of the formula $N(CH_2CH_2CH_2SiO_{3/2})_3$, were added to a solution of 2.22 g (5.60 millimoles) of $WCl_6$ in 75 ml of dry ethanol at room temperature. This suspension was stirred first for 1 hour at room temperature and then for 24 hours under reflux. The solid was then filtered off, extracted with dry ethanol for 4 hours in a Soxhlet extractor, and dried for 4 hours at 100° C./$10^{-1}$ mbar. It was possible to obtain 12.2 g (99.3% of theory) of a bluish green powder. The polymeric metal complex, which consisted of units of the formula $WCl_6[N(CH_2CH_2CH_2SiO_{3/2})_3]_6$ gave the following analytical data:

|  | % C | % H | % N | % W | % Cl |
|---|---|---|---|---|---|
| Theory: | 29.81 | 5.00 | 3.86 | 8.45 | 9.78 |
| Found: | 29.04 | 5.11 | 4.03 | 7.89 | 8.91 |

EXAMPLE 2

A solution of 1.56 g (5.71 millimoles) of $MoCl_5$ in 60 ml of dry chloroform was combined with 12.4 g of a polymeric amine, consisting of units of the formula $(H_3C)N(CH_2CH_2CH_2SiO_{3/2})_2$, and the mixture was stirred first for 1 hour at room temperature and then for 20 hours under reflux. Thereafter, the solid was centrifuged off, extracted with chloroform for 3 hours in a Soxhlet extractor, dried for 6 hours at 80° C./100 mbar, and then ground in a cross-beater mill. The yield of the polymeric molybdenum compound containing units of the formula $MoCl_5[(H_3C)N(CH_2CH_2CH_2SiO_{3/2})_2]_{10}$ was 13.9 g (99.5% of theory).

|  | Analytical data: | | | | |
|---|---|---|---|---|---|
|  | % C | % H | % N | % Mo | % Cl |
| Theory: | 34.36 | 6.18 | 5.72 | 3.92 | 7.24 |
| Found: | 33.28 | 6.27 | 5.91 | 3.27 | 7.98 |

EXAMPLE 3

2.0 g (5.68 millimoles) of $W(CO)_6$ and 38.8 g of a polymeric amine containing units of the formula

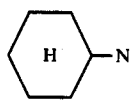

$[(CH_2)_5SiO_{3/2}]_2$ in 250 ml of boiling toluene were brought to reaction for 30 hours. Thereafter, the solid was centrifuged off from the liquid phase, extracted with toluene for 6 hours. and then dried for 4 hours at 120° C./$10^{-1}$ mbar. It was possible to obtain 40.5 g of an ochre-colored solid. Assuming that a polymer system containing units of the formula $W(CO)_5\{$

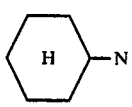

$[(CH_2)_5SiO_{3/2}]_2\}_{20}$ had been formed, the yield was 99.6% of theory. The following analytical data were to be expectd:

| % C | % H | % Si | % N | % W |
|---|---|---|---|---|
| 54.55 | 8.73 | 15.70 | 3.91 | 2.57 | the following were found:

| % C | % H | % Si | % N | % W |
|---|---|---|---|---|
| 53.89 | 8.60 | 14.94 | 4.07 | 2.31 |

EXAMPLE 4

3.0 g (19.87 millimoles) of $MnSO_4$ were reacted with 20.62 g of a polymeric amine consisting of units of the formula $(C_8H_{17})N(CH_2SiO_{3/2})_2$ in 100 ml of boiling methanol for 48 hours.

After the reaction mixture had been worked up as described in Example 1, it was possible to obtain 23.3 g (98.6% of theory) of a polymeric manganese compound containing units of the formula $MnSO_4[(C_8H_{17})N(CH_2SiO_{3/2})_2]_4$.

|  | Analytical data: | | | | |
|---|---|---|---|---|---|
|  | % C | % H | % N | % Mn | % $SO_4$ |
| Theory: | 40.41 | 7.12 | 4.71 | 4.62 | 8.08 |
| Found: | 39.07 | 7.51 | 5.10 | 4.55 | 7.87 |

EXAMPLE 5

1.2 g (3.30 millimoles) of $ReCl_5$ and 6.7 g of a polymeric amine containing units of the formula:

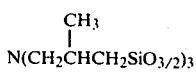

were stirred in dry boiling ethanol for 20 hours. After the reaction mixture had been worked up as described in Example 1, 7.69 g (97.3% of theory) of a polymeric rhenium compound consisting of

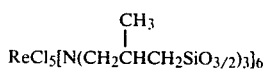

were obtained.

| | Analytical data: | | | | |
|---|---|---|---|---|---|
| | % C | % H | % N | % Fe | % Cl |
| Theory: | 36.11 | 6.06 | 3.51 | 7.77 | 7.40 |
| Found: | 34.99 | 6.00 | 3.46 | 7.41 | 7.27 |

EXAMPLE 6

11.19 g (99.3% of theory) of a polymeric iron compound consisting of units of the formula $FeSO_4\{N[(CH_2)_3SiO_{3/2}]_3\}_4$ were prepared from 2.34 g (8.42 millimoles) of $FeSO_4.7H_2O$ and 10 g of polymeric amine containing units of the formula $N(CH_2CH_2CH_2SiO_{3/2})_3$, analogously to Example 1, after reaction for 24 hours in 100 ml of boiling methanol.

| | Analytical data: | | | | |
|---|---|---|---|---|---|
| | % C | % H | % N | % Fe | % SO_4 |
| Theory: | 32.32 | 5.42 | 4.19 | 4.17 | 7.18 |
| Found: | 31.28 | 5.55 | 4.95 | 3.74 | 6.80 |

EXAMPLE 7

29.04 g (95.5% of theory) of a purple-colored polymer product of the theoretical composition $CoCl_2\{N[(CH_2)_3SiO_{3/2}]_3\}_{25}$ were synthesized from 0.96 g (4.03 millimoles) of $CoCl_2.6H_2O$ and 29.9 g of a polymeric amine containing units of the formula $N(CH_2CH_2CH_2SiO_{3/2})_3$, analogously to Example 1, after stirring for 24 hours in 200 ml of boiling ethanol.

| | Analytical data: | | | | |
|---|---|---|---|---|---|
| | % C | % H | % N | % Co | % Cl |
| Theory: | 35.83 | 6.01 | 4.64 | 0.78 | 0.94 |
| Found: | 34.17 | 5.98 | 5.63 | 0.78 | 0.61 |

EXAMPLE 8

11.2 g (98.6% of theory) of a polymeric nickel-amine compound, consisting of units of the formula:

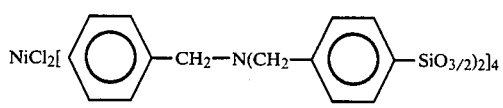

were prepared from 1.6 g (6.73 millimoles) of $NiCl_2.6H_2O$ and 10.5 g of an amine comprising units of the formula:

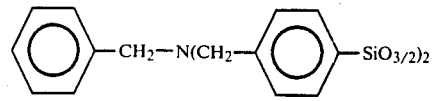

analogously to Example 1, after stirring for 18 hours in 100 ml of refluxing ethanol.

| | Analytical data: | | | | |
|---|---|---|---|---|---|
| | % C | % H | % N | % Ni | % Cl |
| Theory: | 59.78 | 4.54 | 3.32 | 3.48 | 4.20 |
| Found: | 59.01 | 4.77 | 3.63 | 3.09 | 3.99 |

EXAMPLE 9

8.40 g (99.6% of theory) of a polymeric ruthenium-amine compound, consisting of units of the formula $RuCl_3[N(CH_2CH_2CH_2SiO_{3/2})_3]_4$, were obtained from 2.0 g (6.05 millimoles of $RuCl_3(CH_2CN)_3$ and 7.17 g of a polymeric amine comprising units of the formula $N(CH_2CH_2CH_2SiO_{3/2})_3$, analogously to Example 1, after stirring for 20 hours in 150 ml of boiling toluene.

| | Analytical data: | | | | |
|---|---|---|---|---|---|
| | % C | % H | % N | % Ru | % Cl |
| Theory: | 31.03 | 5.21 | 4.02 | 7.25 | 7.63 |
| Found: | 30.48 | 5.37 | 3.96 | 6.85 | 6.89 |

EXAMPLE 10

9.98 g (98.0% of theory) of a polymeric rhodium-amine complex compound, consisting of units of the theoretical empirical formula $RhCl_3\{N(CH_2CH_2CH_2SiO_{3/2})_3\}_{50}$, were obtained from 0.225 g (0.677 millimole) of $RhCl_3(CH_3CN)_3$ and 10.0 g of a polymeric amine containing units of the formula $N(CH_2CH_2CH_2SiO_{3/2})_3$, analogously to Example 1, after stirring for 24 hours in 150 ml of boiling toluene.

| | Analytical data: | | | | |
|---|---|---|---|---|---|
| | % C | % H | % N | % Rh | % Cl |
| Theory: | 35.93 | 6.03 | 4.66 | 0.68 | 0.71 |
| Found: | 34.71 | 6.24 | 4.89 | 0.71 | 0.88 |

EXAMPLE 11

0.466 g (1.40 millimoles) of $RhCl_3(CH_3CN)_3$ was reacted with 25.0 g of a polymeric, $SiO_2$-crosslinked amine, consisting of units of the formula $N(CH_2CH_2CH_2SiO_{3/2})_3.SiO_2$, analogously to Example 10. It was possible to obtain 24.5 g (96.9% of theory) of an $SiO_2$-crosslinked, polymeric rhodium-amine compound, consisting of units of the empirical formula $RhCl_3\{N(CH_2CH_2CH_2SiO_{3/2})_3.SiO_2\}_{50}$.

| | Analytical data: | | | | |
|---|---|---|---|---|---|
| | % C | % H | % N | % Rh | % Cl |
| Theory: | 29.96 | 5.03 | 3.88 | 0.57 | 0.59 |
| Found: | 29.02 | 5.42 | 4.21 | 0.57 | 0.65 |

EXAMPLE 12

5 g of a polymeric rhodium-amine complex compound which was prepared analogously to Example 10 and consisted of units of the formula $RhCl_3\{N(CH_2CH_2CH_2SiO_{3/2})_3\}_5$ were suspended in 70 ml of dry ethanol at room temperature. A solution of 1 g (14.69 millimoles) of sodium methylate in 50 ml of ethanol was added dropwise to this suspension in the course of 15 minutes. The mixture was stirred after 30 minutes at room temperature and then 4 hours under reflux. Thereafter, the resulting dark brown solid was filtered off, extracted with an alcohol/water mixture (1:1A) for 4 hours in a Soxhlet extractor, and dried for 4 hours at 80° C./$10^{-1}$ mbar. It was possible to obtain 5.05 g of a modified polymeric rhodium-amine complex compound, the chloride content of which was substantially reduced compared to the starting value.

|  | Analytical data: | | | | |
|---|---|---|---|---|---|
|  | % C | % H | % N | % Rh | % Cl |
| Starting material | 30.07 | 5.42 | 4.26 | 6.13 | 6.28 |
| Found: | 33.42 | 6.00 | 4.12 | 5.91 | 0.36 |

EXAMPLE 13

5 g of a polymeric rhodium-amine complex compound prepared analogously to Example 10 and consisting of units of the formula $RhCl_3\{N(CH_2CH_2CH_2SiO_{3/2})_3\}_{10}$ were suspended in 50 ml of toluene under an $N_2$ protective gas atmosphere. After 0.826 g of triphenylphosphine had been added, the mixture was stirred for 3 hours under reflux. The mixture was filtered and the residual solid was washed with twice 30 ml of toluene, extracted with ethanol for 3 hours in a Soxhlet extractor, and dried for 3 hours at 100° C./$10^{-1}$ mbar. The 4.9 g of polymeric product obtained had a phosphorus content of 0.87%, an Rh content of 2.83% and a chloride iof 1.34% according to analyses, indicating reduction and phosphine addition.

EXAMPLE 14

5 g of a polymeric rhodium-amine complex compound prepared analogously to Example 10 and consisting of units of the formula $RhCl_3\{N(CH_2CH_2CH_2SiO_{3/2})_3\}_{10}$ were suspended in 50 ml of ethanol. First 3.20 g of a 37% strength formaldehyde solution diluted with 10 ml of ethanol, and thereafter 0.30 g of sodium borohydride, dissolved in 15 ml of ethanol, were added dropwise to this suspension, which was heated at the reflux temperature. The mixture was stirred for a further 2 hours under reflux, and was then filtered, and the residue was extracted with ethanol for 4 hours in a Soxhlet extractor. After drying for 4 hours at 100° C./$10^{-1}$ mbar, 4.6 g of a modified, polymeric rhodium-amine complex compound were obtained. The modification achieved can be shown by the comparison, below, of the chloride analyses of the starting compound and of the product.

|  | Analytical data: | | | | |
|---|---|---|---|---|---|
|  | % C | % H | % N | % RH | % Cl |
| Starting material | 33.12 | 5.85 | 4.71 | 3.05 | 3.20 |
| Found: | 33.89 | 5.72 | 4.63 | 3.20 | 1.26 |

EXAMPLE 15

2.0 g (4.53 millimoles) of

were dissolved in 75 ml of ethanol at room temperature. After the addition of 9.85 g of a polymeric amine, consisting of units of the formula $(H_3C)N(CH_2CH_2CH_2SiO_{3/2})_2$, this mixture was first stirred for 2 hours at room temperature and then for 20 hours under reflux. The resulting brown solid was filtered off, extracted with ethanol for 4 hours, and dried for 12 hours at 100° C./100 mbar. It was possible to obtain 11.2 g (94.5% of theory) of a polymeric rhodium-amine complex compound, consisting of units of the empirical formula:

$$Rh(OCCH_3)_2[(H_3C)N(CH_2CH_2CH_2SiO_{3/2})_2]_5$$

|  | Analytical data: | % C | % H | % N | % Rh |
|---|---|---|---|---|---|
| Theory: |  | 35.82 | 6.24 | 5.35 | 7.87 |
| Found: |  | 35.07 | 6.41 | 5.87 | 7.55 |

EXAMPLE 16

200 g (0.317 mole) of a monomeric amine of the formula $N[CH_2LCH_2LCH_2Si(OC_2H_5)_3]_3$ and 14.85 g of a 70% strength solution of tetrapropyl zirconate in propanol were combined in 200 ml of ethanol. The mixture was heated to 60° C., and 100 ml of demineralized water were added to it, in portions, at this temperature. The precipitate which forms after a short time was stirred under reflux for a further 2 hours, filtered off, washed with 0.5 liter of ethanol and 1 liter of $H_2O$, dried for 5 hours at 150° C./100 bar, heated for 24 hours at 250° C./100 mbar, and then ground in a pinned disk mill. It was possible to obtain 94.5 g (96.5% of theory) of a $ZrO_2$-crosslinked amine, consisting of units of the formula $N(CH_2CH_2CH_2SiO_{3/2})_3.0.1ZrO_2$.

|  | Analytical data: | | | | |
|---|---|---|---|---|---|
|  | % C | % H | % N | % Si | % Zr |
| Theory: | 35.00 | 5.88 | 4.54 | 27.28 | 2.95 |
| Found: | 34.76 | 6.04 | 4.90 | 26.70 | 2.79 |

10.0 g of the polymeric amine obtained as described above were combined with a solution of 4.76 g (16.19 millimoles) of $Na_2PdCl_4$ in 100 ml of methanol. Thereafter, the mixture was stirred under reflux for 24 hours. The resulting solid was filtered off, extracted with a methanol/water mixture (1:1) for 4 hours in a Soxhlet extractor, and then dried for 5 hours at 120° C./$10^{-1}$ mbar. It was possible to obtain 12.3 g (95.6% of theory) of a polymeric, $ZrO_2$-crosslinked palladium-amine compound, consisting of units of the formula:

|  | Analytical data: | | | | | |
|---|---|---|---|---|---|---|
|  | % C | % H | % N | % Zr | % Pd | % Cl |
| Theory: | 27.20 | 4.56 | 3.52 | 2.29 | 13.38 | 8.92 |
| Found: | 26.45 | 4.41 | 3.80 | 2.04 | 12.51 | 8.59 |

EXAMPLE 17

3 g of the polymeric palladium-amine complex prepared according to Example 16 were suspended in 50 ml of dry ethanol. A solution of 0.8 g of sodium borohydride in 30 ml of ethanol was added dropwise to this suspension in the course of 15 minutes. The mixture was stirred for 1 hour at room temperature and then 1 hour under reflux. The solid was filtered off, extracted with an ethanol/water mixture (1:1) for 3 hours, and dried for 3 hours at 120° C./$10^{-1}$ mbar.

|  | Analytical data: | | |
|---|---|---|---|
|  | % Pd | % Cl | % N |
| Before reduction: | 12.51 | 8.59 | 3.80 |
| After reduction: | 13.20 | 0.72 | 4.21 |

EXAMPLE 18

11.48 g (98.4% of theory) of a polymeric osmium-amine compound, consisting of units of the formula $OsCl_3[N(CH_2CH_2CH_2SiO_{3/2})_3]_6$, were obtained from 1.67 g (5.62 millimoles of $OsCl_3$ and 10 g of a polymeric amine containing units of the formula $N(CH_2CH_2CH_2SiO_{3/2})_3$, analogously to Example 1, after stirring for 24 hours in 75 ml of boiling methanol.

|  | Analytical Data: | | | | |
|---|---|---|---|---|---|
|  | % C | % H | % N | % Os | % Cl |
| Theory: | 31.25 | 5.24 | 4.05 | 9.16 | 5.12 |
| Found: | 30.55 | 5.10 | 4.26 | 8.79 | 4.97 |

EXAMPLE 19

6.4 g (99.9% of theory) of a yellow polymeric iridium-amine compound, consisting of units of the formula $IrCl_3\{N(CH_2CH_2CH_2SiO_{3/2})_3\}_3$, were obtained from 2.275 g (5.39 millimoles) of $IrCl_3(CH_3CN)_3$ and 4.80 g of a polymeric amine consisting of units of the formula $N(CH_2CH_2CH_2SiO_{3/2})_3$ analogously to Example 10, after stirring for 24 hours in 75 ml of boiling toluene.

|  | Analytical data: | | | | |
|---|---|---|---|---|---|
|  | % C | % H | % N | % Ir | % Cl |
| Theory: | 27.30 | 4.58 | 3.54 | 16.18 | 8.95 |
| Found: | 26.81 | 4.72 | 3.59 | 15.30 | 8.64 |

EXAMPLE 20

14.1 g (97.4% of theory) of a polymeric platinum-amine compound, comprising units of the formula $PtCl_2[N(CH_2CH_2CH_2SiO_{3/2})_3]_2$ were obtained from 7.00 g (16.86 millimoles) of $K_2PtCl_4$ and 10.0 g of a polymeric amine comprising units of the formula $N(CH_2CH_2CH_2SiO_{3/2})_3$, analogously to Example 16, after stirring for 24 hours in 120 ml of boiling ethanol.

|  | Analytical data: | | | | |
|---|---|---|---|---|---|
|  | % C | % H | % N | % Pt | % Cl |
| Theory: | 25.17 | 4.22 | 3.26 | 22.71 | 8.25 |
| Found: | 25.07 | 4.39 | 3.52 | 20.98 | 8.04 |

EXAMPLE 21

21.4 g (96.1% of theory) of an ochre-colored polymeric copper-amine compound comprising units of the formula $CuCl_2[N(CH_2CH_2CH_2SiO_{3/2})_3]_4$ were obtained from 2.875 g (16.86 millimoles) of $CuCl_2.2H_2O$ and 20 g of a polymeric amine consisting of units of the formula $N(CH_2CH_2CH_2SiO_{3/2})_3$, analogously to Example 1, after stirring for 24 hours in 150 ml of boiling ethanol.

|  | Analytical data: | | | | |
|---|---|---|---|---|---|
|  | % C | % H | % N | % Cu | % Cl |
| Theory: | 32.75 | 5.50 | 4.24 | 4.81 | 5.37 |
| Found: | 30.99 | 4.98 | 5.06 | 4.43 | 4.96 |

EXAMPLE 22

12.2 g (97.1% of theory) of a polymeric gold-amine compound comprising units of the formula $AuCl_3[N(CH_2CH_2CH_2SiO_{3/2})_3]_4$ were obtained from 2.56 g (8.44 millimoles) of $AuCl_3$ and 10.0 g of a polymeric amine consisting of units of the formula $N(CH_2CH_2CH_2SiO_{3/2})_3$, analogously to Example 1, after stirring for 24 hours in 120 ml of boiling ethanol.

|  | Analytical data: | | | | |
|---|---|---|---|---|---|
|  | % C | % H | % N | % Au | % Cl |
| Theory: | 29.03 | 4.87 | 3.76 | 13.23 | 7.14 |
| Found: | 28.84 | 4.94 | 3.89 | 12.51 | 7.02 |

EXAMPLE 23

12.5 g (97.2% of theory) of a polymeric silver-amine compound consisting of units of the formula $AgNO_3[N(CH_2CH_2CH_2SiO_{3/2})_3]_2$ were obtained from 2.86 g (16.84 millimoles) of $AgNO_3$ and 10.0 g of a polymeric amine consisting of units of the formula $N(CH_2CH_2CH_2SiO_{3/2})_3$, analogously to Example 1, after stirring for 24 hours in 80 ml of a methanol/water mixture (1:1) heated at the reflux temperature.

|  | Analytical data: | | | | |
|---|---|---|---|---|---|
|  | % C | % H | % total N | % Ag | % $NO_3$ |
| Theory: | 28.34 | 4.76 | 5.51 | 14.14 | 8.13 |
| Found: | 27.59 | 4.83 | 5.76 | 13.95 | 7.99 |

EXAMPLE 24

10 g of the polymeric-amine compound prepared according to Example 7 and consisting of units of the theoretical composition $CoCl_2\{N[(CH_2)_3SiO_{3/2}]_3\}_{25}$ were combined with 44.07 mg (0.133 millimole) of $RhCl_3(CH_3CN)_3$ in 100 ml of toluene. The mixture was stirred under reflux for 24 hours, and thereafter the polymeric solid was filtered off, extracted with toluene for 4 hours in a Soxhlet extractor, and dried for 6 hours at 150° C./100 mbar. It was possible to obtain 9.9 g (98.7% of theory) of a polymeric multi-metal-amine compound consisting of units of the formula;

$0.1RhCl_3.CoCl_2[N(CH_2CH_2CH_2SiO_{3/2})_3]_{25}$

| | Analytical data: | | | |
|---|---|---|---|---|
| | % N | % Co | % Rh | % Cl |
| Theory: | 4.63 | 0.78 | 0.14 | 1.08 |
| Found: | 4.83 | 0.75 | 0.13 | 0.98 |

EXAMPLE 25

10 g of a polymeric iron compound prepared according to Example 6 and containing units of the formula $FeSO_4[N(CH_2CH_2CH_2SiO_{3/2})_3]_4$ were combined with 2.04 g (7.47 millimoles) of $MoCl_5$ in 70 ml of dry chloroform. The mixture was stirred under reflux for 24 hours, and thereafter the polymeric solid was filtered off, extracted with chloroform for 4 hours, and dried for 4 hours at 100° C./$10^{-1}$ mbar. It was possible to obtain 11.7 g (97.2% of theory) of a polymeric multi-metal-amine compound consisting of units of the formula $MoCl_5 \cdot FeSO_4[N(CH_2CH_2CH_2SiO_{3/2})_3]_4$.

| | Analytical data: | | | | |
|---|---|---|---|---|---|
| | % N | % Fe | % Mo | % Cl | % $SO_4$ |
| Theory: | 3.48 | 3.47 | 5.95 | 11.00 | 5.96 |
| Found: | 3.59 | 3.41 | 5.78 | 10.76 | 5.81 |

EXAMPLE 26

2.80 g of $K_2PtCl_4$, 1.837 g of $RhCl_3 \cdot 3.5H_2O$ and 20 g of a polymeric amine consisting of units of the formula $N(CH_2CH_2CH_2SiO_{3/2})_3$ were combined in 150 ml of ethanol. The mixture was stirred under reflux for 24 hours, and then worked up analogously to Example 1. It was possible to obtain 22.9 g (98.7% of theory) of a polymeric platinum-rhodium-amine compound consisting of units of the formula:

$PtCl_2 \cdot RhCl_3[N(CH_2CH_2CH_2SiO_{3/2})_3]_{10}$

| | Analytical data: | | | |
|---|---|---|---|---|
| | % N | % Pt | % Rh | % Cl |
| Theory: | 4.07 | 5.67 | 2.99 | 5.15 |
| Found: | 4.24 | 5.39 | 2.87 | 5.02 |

EXAMPLE 27

By stepwise reaction of 10 g of a polymeric iron compound, prepared analogously to Example 6 and consisting of units of the formula $FeSO_4[N(CH_2CH_2CH_2SiO_{3/2})_3]_{15}$, with 0.52 g of $NiCl_2 \cdot 6H_2O$ in 100 ml of ethanol, analogously to Example 8, and of the resulting product with 0.59 g of $MoCl_5$, analogously to Example 25, 10.6 g (97.5% of theory) of a polymeric iron-nickel-molybdenum compound containing units of the formula $FeSO_4 \cdot NiCl_2 \cdot MoCl_5[N(CH_2CH_2CH_2SiO_{3/2})_3]_{15}$ were obtained.

| | Analytical data: | | | | | |
|---|---|---|---|---|---|---|
| | % N | % Fe | % Ni | % Mo | % Cl | % $SO_4$ |
| Theory: | 4.20 | 1.12 | 1.17 | 1.92 | 4.96 | 1.92 |
| Found: | 4.46 | 1.07 | 1.10 | 1.84 | 4.80 | 1.74 |

EXAMPLE 28

A mixture of 3.022 g of the polymeric cobalt-amine compound prepared according to Example 7 and having a cobalt content of 0.78%, 50 ml (0.4 mole) of hex-1-ene and 100 ml of toluene, in a 500 ml agitatory autoclave, was subjected to a $CO/H_2$ (1:1) pressure of 200 bar when cold. In the course of 2.5 hours, at a temperature of 165° C., about 90% of the hex-1-ene employed was converted into n-heptanal and 2-methylhexanal. It was possible to determine the composition of the resulting products by gas chromatography to be about 50% of n-heptanal, 40% of 2-methylhexanal, 1% of n-heptanol, 1% of 2-methylhexanol and 8% of hexane, in addition to unreacted hex-1-ene.

After this reaction, the catalyst was filtered off, washed with twice 50 ml of toluene and reused for the hydroformylation of hex-1-ene analogously to the above description.

In this cycle, about 89% of the hex-1-ene was converted to n-heptanal and 2-methylhexanal in the course of 2.5 hours. It was possible to determine the composition of the products by gas chromatogrphy to be about 52% of n-heptanal, 37% of 2-methylhexanal, 2% of n-heptanol, 1% of 2-methylhexanol and 8% of hexane, in addition to unreacted hex-1-ene.

EXAMPLE 29

7.22 g of the $SiO_2$-crosslinked polymeric rhodium-amine compound prepared according to Exampl 11 were first heated for 48 hours at 220° C./100 mbar in a vacuum drying cabinet. Thereafter, this heated product together with 300 ml of hex-1-ene, in a 500 ml agitatory autoclave, was subjected to a $CO/H_2$ (1:1) pressure of 200 bar when cold, at a temperature of 110° C. Each pressure drop of 50 bar was again compensated by forcing in $CO/H_2$. After 6 hours reaction time, no further gas absorption was detectable. The autoclave was cooled, the $CO/H_2$ pressure was released, and a gas chromatographic investigation of the product was carried out. According to this analysis, approximately 97% conversion of the hex-1-ene to the desired aldehydes n-heptanal and 2-methylhexanal in the ratio of 52:48 had taken place.

Thereafter, the liquid phase was separated off from the solid catalyst residue and, after the addition of a further 300 ml of hex-1-ene, a further hydroformylation according to the above scheme, but in this case at a temperature of 170° C., was carried out. After 7 hours reaction time, gas chromatographic investigation again indicated approximately 97% hydroformylation of the hex-1-ene and a partial further hydrogenation of the aldehydes formed. The exact product distribution was 3% of hexane, 6% of n-heptanal, 10% of 2-methylhexanal, 33% of n-heptanol and 48% of 2-methylhexanol.

EXAMPLE 30

The palladium catalyst after-treated according to Example 17 and containing 13.20% of palladium was employed for the hydrogenation of the model substance ethyl acrylate. For this purpose, 32.2 mg of this catalyst were combined with 4.36 ml of ethyl acrylate and 20 ml of toluene in a 50 ml glass flask connected to a glass hydrogenation apparatus. With magnetic stirring, under an $H_2$ pressure of about 1 bar and at a temperature of 80°±2° C., the ethyl acrylate employed was converted quantitatively, in the course of 85 minutes, to ethyl propionate, as could be determined from the amount of hydrogen absorbed and from the gas chromatographic investigation of the reaction product.

The catalyst was then filtered off, washed out with twice 20 ml of toluene, and reused for the hydrogenation of ethyl acrylate according to the above scheme, and it was possible to obtain quantitative hydrogenation in the course of 80 minutes.

In this manner, the catalyst employed was separated off and reused 5 times altogether, without it being possible to detect any loss in activity.

EXAMPLE 31

The polymeric platinum-amine catalyst prepared according to Example 20 was employed for trichlorosilane addition to allyl chloride. For this purpose, 55.8 mg of this compound were suspended in 24.4 ml of allyl chloride, and 30.3 ml of trichlorosilane were added dropwise in the course of 1 hour at room temperature, while stirring vigorously. Thereafter, the mixture was heated under reflux for 3 hours. In the course of this time, the boiling point at the bottom increased from 38° C. to far above 100° C. An investigation of the liquid phase by NMR spectroscopy showed that it consisted of about 95% of the desired γ-chloropropyltrichlorosilane, and that only about 5% of unreacted allyl chloride was present.

EXAMPLE 32

3.23 g off the polymeric rhodium-cobalt-amine compound prepared according to Example 24 were first heated for 48 hours at 270° C./100 mbar in a vacuum drying cabinet. Thereafter, this heated product together with 250 ml of hex-1-ene, in a 500 ml agitator autoclave, was subjected to a $CO/H_2$ (1:1) pressure of 200 bar when cold, and to a temperature of 130° C. Each 50 bar drop in pressure was again compensated by forcing in $CO/H_2$. After 6 hours reaction time, no further gas absorption was detectable. The autoclave was cooled, the $CO/H_2$ pressure was released, and a gas chromatographic investigation of the product was carried out. According to this analysis, an approximately 96% conversion of the hex-1-ene to the desired aldehydes n-heptanal and 2-methylhexanal in a ratio of 45:54 had taken place.

We claim:

1. A process for a catalytic reaction to achieve hydroformylation, hydrogenation or, hydrosilylation, which comprises carrying out said reaction in the presence of a catalyst which is a polymeric complex organosiloxane amine of a member selected from the group consisting of molybdenum, tungsten, manganese, rhenium and a metal of the sub-groups VIII and I of the Periodic Table, wherein at least one amine of the formula:

is bonded coordinately to each central metal atom, the metal:nitrogen atomic ratio is from 1:1 to 1:10^6, any coordination points at the metal atom which are still free are occupied by other electron pair donors, and the required charge compensation is effected by means of an inorganic or organic anion, and in the formula (1) $R^1$ and $R^2$ represent a group of the formula

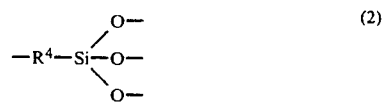

$R^4$ denotes a linear or branched alkylene group having 1 to 10 C atoms or a cycloalkylene group having 5 to 8 C atoms, or represents the units:

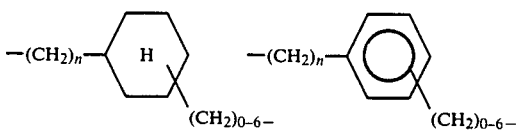

wherein n is 1 to 6 methylene groups linked to a nitrogen atom, $R^1$ and $R^2$ can be identical or different, and the free valences of the oxygen atoms are saturated either by silicon atoms of further groups of the formula (2) and/or by crosslinking bridge members of the formula:

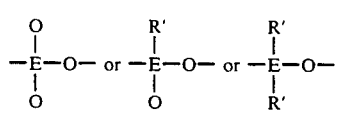

wherein E represents silicon, titanium or zirconium, or by the units:

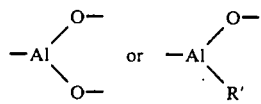

wherein R' is a methyl or ethyl group and the ratio of the silicon atoms in (2) to the bridge atoms silicon, titanium, zirconium and aluminum can be from 1:0 to 1:10, $R^3$ has the same meaning as $R^1$ and $R^2$, or represents hydrogen, a linear or branched alkyl group having 1 to 10 C atoms or a cycloalkyl group having 5 to 8 C atoms or the benzyl group.

2. The process of claim 1, wherein a complex compound of at least one of the selected metals is present along side one another as units in the polymer.

3. The process according to claim 1 for the hydroformylation of an olefin comprising carrying out a hydroformylation reaction of an olefin in the presence of a catalyst which is a polymeric rhodium-amine or cobalt-amine complex and wherein hydrogen and carbon monoxide are present at a total pressure of from 1 to 1000 bar at a temperature from about room temperature to 280°.

4. The process of claim 3, wherein a solubilizer is utilized in the reaction.

5. The process according to claim 1 for hydrogenation of an olefinic compound comprising carrying out a hydrogenation reaction at room temperature up to elevated temperature, under reduced pressure, atmospheric pressure or elevated pressure.

6. The process according to claim 1, wherein the catalyst is a purple colored polymer product of the theoretical composition $CoCl_2\{N[(CH_2)_3SiO_{3/2}]_3\}_{25}$ and the reaction is carried out with an olefin in the presence of an inert solvent to convert the olefin to the corresponding aldehyde.

7. The process according to claim 1, wherein a silica crosslinked polymeric rhodium amine compound having the formula $RhCl_3\{N(CH_2CH_2CH_2SiO_{3/2})_3.SiO_2\}_{50}$ and an olefin are subjected to a carbon monoxide-hydrogen pressure at a temperature of 110° to convert said olefin to the corresponding aldehyde.

8. The process according to claim 7 which further comprises separating off the solid catalyst residue and adding additional olefin to carry out an additional hydroformylation reaction at a temperature of 170° to obtain hydroformylation of the olefin and partial further hydrogenation of the aldehyde product.

9. The process according to claim 1, wherein hydrogenation of ethyl acrylate is carried out in the presence of an inert hydrocarbon solvent and a palladium catalyst which had been obtained by suspending $PdCl_2\{N(CH_2CH_2CH_2SiO_{3/2})_3.0.1ZrO_2\}_2$ in dry ethanol and treating with sodium borohydride at elevated temperature.

10. The process according to claim 1, wherein trichlorosilane is added to allyl chloride in the presence of a catalyst which has the formula $PtCl_2[N(CH_2CH_2CH_2SiO_{3/2})_3]_2$.

11. The process according to claim 1, wherein a catalyst of the formula $0.1RhCl_3.CoCl_2[N(CH_2CH_2CH_2SiO_{3/2})_3]_{25}$ is heated under vacuum conditions and thereafter contacted with an olefin at elevated temperature and pressure in the presence of $CO/H_2$ (1:1) to produce the desired aldehyde.

* * * * *